(12) United States Patent
Mechoulam et al.

(10) Patent No.: US 9,447,019 B2
(45) Date of Patent: Sep. 20, 2016

(54) FLUORINATED CBD COMPOUNDS, COMPOSITIONS AND USES THEREOF

(71) Applicants: YISSUM RESEARCH DEVELOPMENT COMPANY OF THE HEBREW UNIVERSITY OF JERUSALEM LTD, Jerusalem (IL); UNIVERSIDADE DE SAO PAULO-USP, Sao Paulo (BR); UNIVERSIDADE FEDERAL DO RIO GRANDE DO SUL-UFRGS, Porto Alegre (BR)

(72) Inventors: Raphael Mechoulam, Jerusalem (IL); Antonio Waldo Zuardi, Ribeirao Preto (BR); Flavio Pereira Kapczinski, Porto Elegre (BR); Jaime Eduardo Cecilio Hallak, Ribeirao Preto (BR); Francisco Silveira Guimaraes, Sao Paulo (BR); Jose Alexandre de Souza Crippa, Ribeirao Preto (BR); Aviva Breuer, Jerusalem (IL)

(73) Assignees: UNIVERSIDADE DE SAO PAULO-USP, Sao Paulo/SP (BR); UNIVERSIDADE FEDERAL DO RIO GRANDE DO SUL-UFRGS, Porto Alegre-RS (BR); YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 14/759,689

(22) PCT Filed: Jan. 8, 2014

(86) PCT No.: PCT/IL2014/050023
§ 371 (c)(1),
(2) Date: Jul. 8, 2015

(87) PCT Pub. No.: WO2014/108899
PCT Pub. Date: Jul. 17, 2014

(65) Prior Publication Data
US 2015/0344403 A1     Dec. 3, 2015

Related U.S. Application Data

(60) Provisional application No. 61/750,043, filed on Jan. 8, 2013.

(51) Int. Cl.
*A61K 31/055*     (2006.01)
*C07C 39/42*     (2006.01)
(Continued)

(52) U.S. Cl.
CPC ............. *C07C 69/63* (2013.01); *C07C 39/373* (2013.01); *C07C 39/42* (2013.01); *C07C 69/16* (2013.01); *C07C 2101/16* (2013.01)

(58) Field of Classification Search
CPC ...... C07C 69/63; C07C 39/42; A61K 31/055
USPC ........................................ 514/548, 729, 568
See application file for complete search history.

(56) References Cited

U.S. PATENT DOCUMENTS

| 7,105,685 B2 | 9/2006 | Travis |
| 2011/0052694 A1 | 3/2011 | Stinchcomb |

FOREIGN PATENT DOCUMENTS

| WO | 2009018389 A1 | 2/2009 |
| WO | 2011006099 A1 | 1/2011 |

(Continued)

OTHER PUBLICATIONS

Meanwell, N. A., "Synopsis of Some Recent Tactical Application of Bioisosteres in Drug Design", Journal of Medicinal Chemistry, 2011, 54, 2529-2591.

(Continued)

*Primary Examiner* — Kamal Saeed
*Assistant Examiner* — Janet L Coppins
(74) *Attorney, Agent, or Firm* — Cooley LLP

(57) ABSTRACT

The present invention relates to fluorine substituted CBD compounds, compositions thereof and uses thereof for the preparation of medicaments.

10 Claims, 6 Drawing Sheets

(51) Int. Cl.
    *C07C 69/63*     (2006.01)
    *C07C 69/16*     (2006.01)
    *C07C 39/373*     (2006.01)

(56) References Cited

FOREIGN PATENT DOCUMENTS

| WO | WO 2011006099 A1 * | 1/2011 | ............ C07B 57/00 |
| WO | 2012011112 A1 | 1/2012 | |

OTHER PUBLICATIONS

Bohm Hans-Joachim et al., "Fluorine in medicinal chemistry", ChemBioChem, 2004, 5, 637-643.

PCT International Search Report and Written Opinion, PCT Application No. PCT/IL2014/050023, published May 15, 2014, 11 pages.

Campos A. C. et al. "Involvement of 5HT1A receptors in the anxiolytic-like effects of cannabidiol injected into the dorsolateral periaqueductal gray of rats" Psychopharmacology (Burl). 199(2):223-30, 2008.

File S. E. "Behavioural detection of anxiolytic action, in Experimental approaches to anxiety and depression" Elliott J. M. et al. eds; pp. 25-44, Wiley, New York, 1992.

Issy A. C., et al. "Nitric oxide modulation of methylphenidate-induced disruption of prepulse inhibition in Swiss mice" Behav. Brain Res. 205(2):475-81, 2009.

Long L.E., et al. "Cannabidiol Reverses MK-801-Induced Disruption of Prepulse Inhibition in Mice" Neuropsychopharmacology 31:795-803, 2006.

Moreira F.A., et al. "Cannabidiol inhibits the hyperlocomotion induced by psychotomimetic drugs in mice" Eur. J. Pharmacol. 512(2-3):199-205, 2005.

Onaivi E.S., et al. "Pharmacological characterization of cannabinoids in the elevated plus maze" J. Pharmacol. Exp. Ther. 253:1002-9, 1990.

Zanelati T.V., et al. "Antidepressant-like effects of cannabidiol in mice: possible involvement of 5-HT1A receptors" Br. J. Pharmacol. 159:122-8, 2010.

Crocker, P. J., et al. "The Role of Fluorine Substitution in the Structure-Activity Relationships (SAR) of Classical Cannabinoids" Bioorg. Med. Chem. Lett. Mar. 15, 2007; 17(6): 1504-1507.

Nikas, S. P., et al., "The Role of Halogen Substitution in Classical Cannabinoids: A CB1 Pharmacophore Model" The AAPS Journal 6(4) Article 30, pp. 1-12.

Gurney, S. M. R., et al. "Pharmacology, Toxicology, and Adverse Effects of Synthetic Cannabinoid Drugs" Forensic Science Review, Jan. 2014, 26(1): 53-78.

* cited by examiner

FLUORINATED CBD COMPOUNDS, COMPOSITIONS AND USES THEREOF

CROSS-REFERENCE TO RELATED APPLICATION

This application is a U.S. national stage application under 35 U.S.C. §371 of International Application No. PCT/IL2014/050023, filed on Jan. 8, 2014 and entitled "FLUORINATED CBD COMPOUNDS, COMPOSITIONS AND USES THEREOF", which claims the benefit of priority to U.S. Provisional Application No. 61/750,043, filed on Jan. 8, 2013, the contents of each of which are hereby incorporated by reference in their entireties for all purposes.

TECHNOLOGICAL FIELD

The present invention relates to fluorine substituted CBD compounds, compositions thereof and uses thereof for the preparation of medicaments.

PRIOR ART

References considered to be relevant as background to the presently disclosed subject matter are listed below:

REFERENCES

Campos A C, Guimarães F S. Involvement of 5HT1A receptors in the anxiolytic-like effects of cannabidiol injected into the dorsolateral periaqueductal gray of rats. Psychopharmacology (Burl). 199(2):223-30, 2008.

File S E. Behavioural detection of anxiolytic action, in *Experimental approaches to anxiety and depression* (Elliott J M, Heal D J and Marsden C A eds) pp 25-44, Wiley, New York, 1992.

Issy A C, Salum C, Del Bel E A. Nitric oxide modulation of methylphenidate-induced disruption of prepulse inhibition in Swiss mice. Behav Brain Res. 205(2):475-81, 2009.

Long L E, Malone D T, Taylor D A. Cannabidiol Reverses MK-801-Induced Disruption of Prepulse Inhibition in Mice. Neuropsychopharmacology 31:795-803, 2006.

Moreira F A, Guimarães F S. Cannabidiol inhibits the hyperlocomotion induced by psychotomimetic drugs in mice. Eur J Pharmacol. 512(2-3):199-205, 2005.

Onaivi E S, Green M R, Martin B R. Pharmacological characterization of cannabinoids in the levated plus maze J Pharmacol Exp Ther 255:1002-9, 1990.

Paxinos G. and Watson C. *The rat brain in stereotaxic coordinates.* Academic Press, New York, 1997.

Zanelati T V, Biojone C, Moreira F A, Guimarães F S, Joca S R. Antidepressant-like effects of cannabidiol in mice: possible involvement of 5-HT1A receptors. Br J Pharmacol. 159:122-8, 2010.

Acknowledgement of the above references herein is not to be inferred as meaning that these are in any way relevant to the patentability of the presently disclosed subject matter.

GENERAL DESCRIPTION

The present invention provides a compound having the general formula (I):

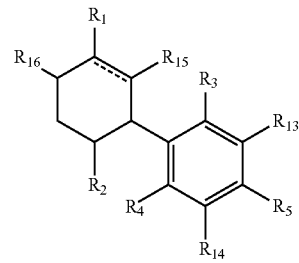

wherein

===== is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(=O)$R_8$, —C(=O)O$R_9$ each optionally substituted by at least one F;

$R_2$ is selected from straight or branched $C_1$-$C_8$ alkyl, straight or branched $C_2$-$C_{10}$ alkenyl, straight or branched $C_2$-$C_{10}$ alkynyl, each optionally substituted by at least one F;

$R_3$ and $R_4$ are each independently selected from H, straight or branched $C_1$-$C_5$ alkyl, —O$R_{10}$, —C(=O)$R_{11}$, —OC(=O)$R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{13}$, $R_{14}$, $R_{15}$ and $R_{16}$ are each optionally selected from H and F;

provided that at least one of $R_{13}$, $R_{14}$, $R_{15}$ and $R_{16}$ is F or at least one of $R_1$ and $R_2$ is substituted with F.

In another one of its aspects the invention provides a compound having the general formula (II):

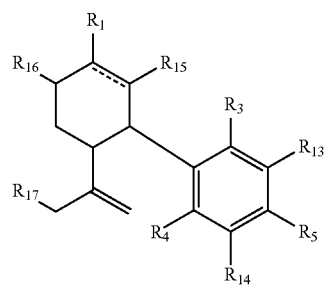

wherein

===== is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(=O)$R_8$, —C(=O)O$R_9$ each optionally substituted by at least one F;

$R_3$ and $R_4$ are each independently selected from H, straight or branched $C_1$-$C_5$ alkyl, —$OR_{10}$, —$C(=O)R_{11}$, —$OC(=O)R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —$NH_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$ alkoxy, —$NH_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —$NH_3$, straight or branched $C_1$-$C_5$ amine;

$R_{13}$, $R_{14}$, $R_{15}$, $R_{16}$ and $R_{17}$ are each optionally selected from H and F;

provided that at least one of $R_{13}$, $R_{14}$, $R_{15}$ and $R_{16}$ is F or $R_1$ is substituted with F.

In another one of its aspects the invention provides a compound having the general formula (III):

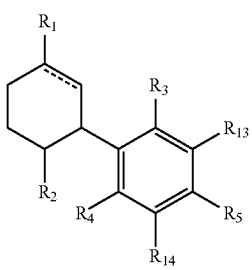

(III)

wherein

===== is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —$C(=O)R_8$, —$C(=O)OR_9$;

$R_2$ is selected from straight or branched $C_1$-$C_8$ alkyl, straight or branched $C_2$-$C_{10}$ alkenyl, straight or branched $C_2$-$C_{10}$ alkynyl;

$R_3$ and $R_4$ are each independently selected from H, straight or branched $C_1$-$C_5$ alkyl, —$OR_{10}$, —$C(=O)R_{11}$, —$OC(=O)R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —$NH_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$ alkoxy, —$NH_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —$NH_3$, straight or branched $C_1$-$C_5$ amine;

$R_{13}$ and $R_{14}$ are each optionally selected from H and F; provided that at least one of $R_{13}$ and $R_{14}$ are F.

In yet a further aspect the invention provides a compound of general formula (IV)

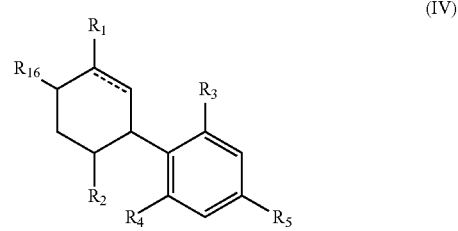

(IV)

wherein

===== is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —$C(=O)R_8$, —$C(=O)OR_9$ each optionally substituted by at least one F;

$R_2$ is selected from straight or branched $C_1$-$C_8$ alkyl, straight or branched $C_2$-$C_{10}$ alkenyl, straight or branched $C_2$-$C_{10}$ alkynyl, each optionally substituted by at least one F;

$R_3$ and $R_4$ are each independently selected from H, straight or branched $C_1$-$C_5$ alkyl, —$OR_{10}$, —$C(=O)R_{11}$, —$OC(=O)R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —$NH_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$ alkoxy, —$NH_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —$NH_3$, straight or branched $C_1$-$C_5$ amine;

$R_{15}$ and $R_{16}$ are each optionally selected from H and F;

provided that at least one of $R_{15}$ and $R_{16}$ is F or at least one of $R_1$ and $R_2$ is substituted with F.

In some embodiments ===== is a double bond.

In some other embodiments $R_1$ straight or branched $C_1$-$C_8$ alkyl; $R_3$ and $R_4$ are each independently —$OR_{10}$; $R_{10}$ is selected from H, a straight or branched $C_1$-$C_5$ alkyl.

In further embodiments $R_1$ is straight or branched $C_1$-$C_8$ alkyl, and $R_3$ and $R_4$ are OH.

In other embodiments, $R_3$ and $R_4$ are each independently selected from H, —$OR_{10}$, and —$OC(=O)R_{12}$; $R_{10}$ is selected from H, a straight or branched $C_1$-$C_5$ alkyl; and $R_{12}$ is selected from H, OH, straight or branched $C_1$-$C_5$ alkyl, —$NH_3$, straight or branched $C_1$-$C_5$ amine.

In some embodiments, $R_5$ is a straight or branched $C_5$-$C_{12}$ alkyl.

In further embodiments of a compound of the invention at least one of $R_{13}$, $R_{14}$, $R_{15}$ and $R_{16}$ is F.

In other embodiments of a compound of the invention at least one of $R_{13}$ and $R_{14}$ is F.

In further embodiments of a compound of the invention at least one of $R_{15}$ and $R_{16}$ is F.

In other embodiments of a compound of the invention at least one of $R_1$ and $R_2$ is substituted with F.

In yet further embodiments of a compound of the invention $R_1$ is selected from straight or branched $C_1$-$C_8$ alkyl, straight or branched $C_2$-$C_{10}$ alkenyl, straight or branched $C_2$-$C_{10}$ alkynyl, each being substituted by F.

In further embodiments of a compound of the invention $R_2$ is selected from straight or branched $C_1$-$C_8$ alkyl, straight or branched $C_2$-$C_{10}$ alkenyl, straight or branched $C_2$-$C_{10}$ alkynyl, each substituted by F.

In further embodiments a compound of the invention is of the general formula (V):

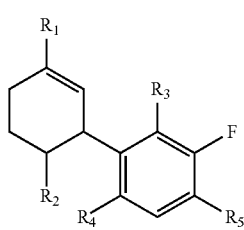

(V)

wherein $R_1$, $R_2$, $R_3$, $R_4$ and $R_5$ are as defined therein.

In other embodiments a compound of the invention is of the general formula (VI):

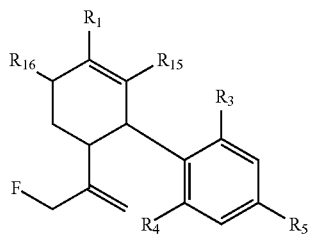

(VI)

wherein $R_1$, $R_3$, $R_4$, $R_5$, $R_{15}$ and $R_{16}$ are as defined therein.

The present invention provides a compound having the general formula (I):

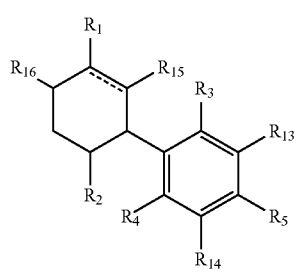

(I)

wherein
----- is a double bond;
$R_1$ is a straight or branched $C_1$-$C_8$ alkyl optionally substituted by at least one F;
$R_2$ is a straight or branched $C_2$-$C_{10}$ alkenyl optionally substituted by at least one F;
$R_3$ and $R_4$ are each independently selected from H, —$OR_{10}$, —OC(=O)$R_{12}$; provided that at least one of $R_3$ and $R_4$ is different than H;
$R_5$ is a straight or branched $C_5$-$C_{12}$ alkyl optionally substituted by at least one substituent selected from —OH, —$NH_3$, straight or branched $C_1$-$C_5$ amine, halogen, phenyl, aryl, heteroaryl, cycloalkyl and heterocycloalkyl;

$R_{10}$ is selected from H, a straight or branched $C_1$-$C_5$ alkyl; and $R_{12}$ is selected from H, OH, straight or branched $C_1$-$C_5$ alkyl, straight or branched $C_1$-$C_5$ alkoxy, —$NH_3$, straight or branched $C_1$-$C_5$ amine;

$R_{13}$, $R_{14}$, $R_{15}$ and $R_{16}$ are each optionally selected from H and F;

provided that at least one of $R_{13}$, $R_{14}$, $R_{15}$ and $R_{16}$ is F or at least one of $R_1$ and $R_2$ is substituted with F.

The invention further provides a compound having the formula:

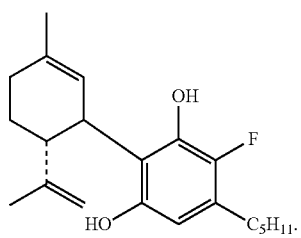

The invention further provides a compound having the formula:

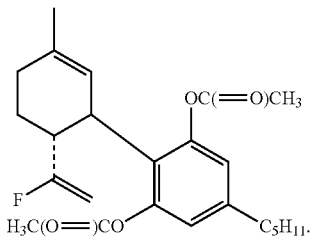

The invention further provides a compound having the formula:

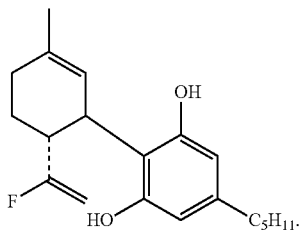

The invention further provides a compound having the formula:

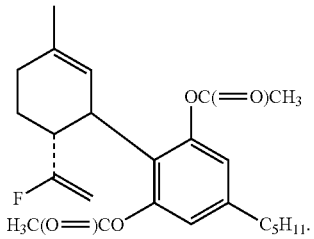

The term "straight or branched $C_1$-$C_8$ alkyl" should be understood to encompass a straight or branched hydrocarbon chain having 1, 2, 3, 4, 5, 6, 7 or 8 carbon atoms, wherein all bonds are single bonds.

The term "straight or branched $C_2$-$C_{10}$ alkenyl" should be understood to encompass a straight or branched hydrocarbon chain having 2, 3, 4, 5, 6, 7, 8, 9 or 10 carbon atoms, having at least one double unsaturated bond between at least two carbon atoms.

The term "straight or branched $C_2$-$C_{10}$ alkynyl" should be understood to encompass a straight or branched hydrocarbon chain having 2, 3, 4, 5, 6, 7, 8, 9 or 10 carbon atoms, having at least one triple unsaturated bond between at least two carbon atoms.

The term "each optionally substituted by at least one F" should be understood to relate to the option of having at least one fluor atom substituted on any of the substituents such as $R_1$ and/or $R_2$ at any position, replacing at least one hydrogen atom.

The term "straight or branched $C_5$-$C_9$ alkoxy" should be understood to encompass a radical of —OR wherein R is a straight or branched alkyl having 5, 6, 7, 8 or 9 carbon atoms.

The term "straight or branched $C_1$-$C_7$ ether" should be understood t encompass a radical of —R'OR wherein R is a straight or branched alkyl having 1, 2, 3, 4, 5, 6 or 7, carbon atoms and R' is a straight or branched alkanyl having 1, 2, 3, 4, 5, 6 or 7, carbon atoms.

The term "straight or branched $C_1$-$C_5$ amine" should be understood to encompass a primary (—$NH_2R$), secondary (—NHRR') or tertiaty amine (—$N^+$RR'R") wherein R, R' and R" are each independently a straight or branched alkyl having 1, 2, 3, 4 or 5 carbon atoms.

The term "halogen" should be understood to encompass any halogen atoms including F, Cl, Br and I.

The term "aryl" is meant to encompass an aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

The term "heteroaryl" refers to a monocyclic or multicyclic aromatic ring system, in certain embodiments, of about 5 to about 15 members wherein one or more, in some embodiments between 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl, The term "cycloalkyl" refers to a monocyclic or multicyclic non-aromatic ring system, in one embodiment of 3 to 10 members, in another embodiment of 4 to 7 members, in further embodiments between 5 to 6 member carbon atoms.

The term "heterocycloalkyl" refers to a monocyclic or multicyclic non-aromatic ring system, in one embodiment of 3 to 10 members, in another embodiment of 4 to 7 members, in a further embodiments between 5 to 6 members, wherein one or more, in certain embodiments between 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidine, or the nitrogen may be quaternary ammonium group where the substituents are selected as above.

When referring to a compound of the invention wherein at least one of $R_{13}$, $R_{14}$, $R_{15}$ and $R_{16}$ is F or at least one of $R_1$ and $R_2$ is substituted with F, it should be understood to encompass a compound of the invention wherein either at least one of $R_{13}$, $R_{14}$, $R_{15}$ and $R_{16}$ is F or at least one of $R_1$ and $R_2$ is a substituent as defined herein above wherein at least one of its hydrogen atoms (at any location on the moiety) is substituted by an F atom.

In some other embodiments at least one of $R_{13}$, $R_{14}$, $R_{15}$ and $R_{16}$ is F and at least one of $R_1$ and $R_2$ is substituted with F. Under this embodiment the invention encompasses a compound wherein at least one of $R_{13}$, $R_{14}$, $R_{15}$ and $R_{16}$ is F and at least one of $R_1$ and $R_2$ is a substituent as defined herein above wherein at least one of its hydrogen atoms (at any location on the moiety) is substituted by an F atom.

In another one of its aspects the invention provides a composition comprising at least one compound of the invention, as described herein above in all aspects and embodiments of a compound of the invention.

In some embodiments of a composition of the invention, said composition is a pharmaceutical composition.

A pharmaceutical composition of the present invention have potent antioxidant and/or free radical scavenging properties, that prevent or reduce oxidative damage in biological systems, such as occurs in ischemic/reperfusion injury, or in chronic neurodegenerative diseases such as Alzheimer's disease, HIV dementia, and many other oxidation associated diseases.

Thus, the invention provides a composition comprising a compound of the invention (as defined in any aspect and embodiment of a compound of the invention) being an antioxidant composition.

As used herein, an "antioxidant" is a substance that, when present in a mixture containing an oxidizable substrate biological molecule, significantly delays or prevents oxidation of the substrate biological molecule. Antioxidants can act by scavenging biologically important reactive free radicals or other reactive oxygen species ($O_2^-$, $H_2O_2$, OH, HOCl, ferryl, peroxyl, peroxynitrite, and alkoxyl), or by preventing their formation, or by catalytically converting the free radical or other reactive oxygen species to a less reactive species.

Relative antioxidant activity can be measured by cyclic voltametry studies, where the voltage (x-axis) is an index of relative antioxidant activity. The voltage at which the first peak occurs is an indication of the voltage at which an electron is donated, which in turn is an index of antioxidant activity.

"Therapeutically effective antioxidant doses" can be determined by various methods, including generating an empirical dose-response curve, predicting potency and efficacy of a congener by using quantitative structure activity relationships (QSAR) methods or molecular modeling, and other methods used in the pharmaceutical sciences. Since oxidative damage is generally cumulative, there is no minimum threshold level (or dose) with respect to efficacy. However, minimum doses for producing a detectable therapeutic or prophylactic effect for particular disease states can be established.

The present invention also relates to pharmaceutical compositions comprising at least one compound of the subject invention in admixture with pharmaceutically acceptable auxiliaries, and optionally other therapeutic agents. The auxiliaries are "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, antioxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

In another one of its aspects that invention provides a compound of the invention, as described herein above in all aspects and embodiments of a compound of the invention, for use in the treatment of at least one condition, disease or disorder selected from the group consisting of:

psychiatric disorders (none limiting examples include: anxiety and stress, depression, schizophrenia, panic, withdrawal symptoms in cannabis and tobacco addiction, reward-facilitating effect of morphine and cocaine, lowers cannabis and THC effects such as memory loss, psychotic-like symptoms);

inflammation (none limiting examples include: Crohn's disease, inflammatory bowel disease, colitis, pancreatitis, asthma, chronic inflammatory and neuropathic pain);

oxidative associated diseases, conditions or disorders (pathological conditions that result at least in part from the production of or exposure to free radicals, particularly oxyradicals, or reactive oxygen species. It is evident to those of skill in the art that most pathological conditions are multi-factorial, and that assigning or identifying the predominant causal factors for any particular condition is frequently difficult. For these reasons, the term "free radical associated disease" encompasses pathological states that are recognized as conditions in which free radicals or reactive oxygen species (ROS) contribute to the pathology of the disease, or wherein administration of a free radical inhibitor (e.g. desferroxamine), scavenger (e.g. tocopherol, glutathione) or catalyst (e.g. superoxide dismutase, catalase) is shown to produce detectable benefit by decreasing symptoms, increasing survival, or providing other detectable clinical benefits in treating or preventing the pathological state. Oxidative associated diseases include, without limitation, free radical associated diseases, such as ischemia, ischemic reperfusion injury, inflammatory diseases, systemic lupus erythematosis, myocardial ischemia or infarction, cerebrovascular accidents (such as a thromboembolic or hemorrhagic stroke) that can lead to ischemia or an infarct in the brain, operative ischemia, traumatic hemorrhage (for example a hypovolemic stroke that can lead to CNS hypoxia or anoxia), spinal cord trauma, Down's syndrome, Crohn's disease, autoimmune diseases (e.g. rheumatoid arthritis or diabetes), cataract formation, uveitis, emphysema, gastric ulcers, oxygen toxicity, neoplasia, undesired cellular apoptosis, radiation sickness, and others. The present invention is further directed to a compound or composition of the invention used in the treatment of oxidative associated diseases of the CNS. In some embodiments, the pharmaceutical composition of the present invention is used for preventing, arresting, or treating neurological damage in Parkinson's disease, Alzheimer's disease and HIV dementia; autoimmune neurodegeneration of the type that can occur in encephalitis, and hypoxic or anoxic neuronal damage that can result from apnea, respiratory arrest or cardiac arrest, and anoxia caused by drowning, brain surgery or trauma (such as concussion or spinal cord shock)).

rheumatoid arthritis;

cardiovascular diseases (none limiting examples include: reduces infarct size and increase blood flow in stroke; reduces vasoconstriction; lowers vascular damage caused by a high glucose environment; reduces the vascular hyperpermeability);

obesity (none limiting examples include: food consumption; lowering appetite); metabolic syndrome);

diabetes and associated disorders and symptoms (none limiting examples include: type 1 and type 2, cardiomyopathy and retinopathy associated with diabetes);

emesis and nausea;

ischemic/reperfusion injury associated with myocardial;

liver or renal diseases;

hypoxia/ischemia injury;

neuronal damage due to neurological diseases or injury (none limiting examples include: Parkinson's disease; Huntington's disease; Alzheimer's disease; cerebral infarction; hepatic encephalopathy; traumatic brain injury; cerebral ischemia; spinal cord injury; memory rescuing effects);

cancer and resistance to cancer chemotherapy (none limiting examples include: cancer cell migration (metastasis); inhibits angiogenesis);

epilepsy and convulsions;

and any condition or symptom associated therefrom.

In further embodiments, said condition, disease, disorder or symptom associated with inflammation is selected from rheumatoid arthritis, multiple sclerosis, inflammatory bowel disease, diabetes and any combinations thereof.

In yet other embodiments, said disease is a psychiatric disease condition or disorder or any symptom associated therewith.

In other embodiments, said psychiatric disease condition or disorder or any symptom associated therewith is selected from anxiety, stress, depression, schizophrenia, panic, substance abuse withdrawal symptoms, reward-facilitating effect of addictive substances, memory loss, psychotic-like symptoms associated with the use of substance abuse.

In another one of its aspects the invention provides a compound of the invention, as described herein above in all aspects and embodiments of a compound of the invention, for use in reduction of oxidative stress.

When referring to "reduction of oxidative stress" it should be understood to encompass any qualitative or quantitative reduction in the oxidative stress in a body tissue or cell of a subject treated with a compound or composition of the invention. Oxidative stress is characterized by an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA. Further, some reactive oxidative species act as cellular messengers in redox signaling. Thus, oxidative stress can cause disruptions in normal mechanisms of cellular signaling.

Non limiting list of diseases, conditions or disorders associated with oxidative stress in a cell or tissue of a subject include: cancer, Parkinson's disease, Alzheimer's disease, atherosclerosis, heart failure, myocardial infarction, Schizophrenia, Bipolar disorder, fragile X syndrome, Sickle Cell Disease, lichen planus, vitiligo, autism, and chronic fatigue syndrome.

In a further aspect the invention provides a compound of the invention, as described herein above in all aspects and embodiments of a compound of the invention, for use in the treatment of any disease, condition or disorder caused by or associated with oxidative stress.

Oxidative associated diseases include, without limitation, free radical associated diseases, such as ischemia, ischemic reperfusion injury, inflammatory diseases, systemic lupus erythematosis, myocardial ischemia or infarction, cerebrovascular accidents (such as a thromboembolic or hemorrhagic stroke) that can lead to ischemia or an infarct in the brain, operative ischemia, traumatic hemorrhage (for example a hypovolemic stroke that can lead to CNS hypoxia or anoxia), spinal cord trauma, Down's syndrome, Crohn's disease, autoimmune diseases (e.g. rheumatoid arthritis or diabetes), cataract formation, uveitis, emphysema, gastric ulcers, oxygen toxicity, neoplasia, undesired cellular apoptosis, radiation sickness, and others. The present invention is believed to be particularly beneficial in the treatment of oxidative associated diseases of the CNS, because of the ability of the cannabinoids to cross the blood brain barrier and exert their antioxidant effects in the brain. In some embodiments, the pharmaceutical composition or compound of the present invention is used for preventing, arresting, or treating neurological damage in Parkinson's disease, Alzheimer's disease and HIV dementia; autoimmune neurodegeneration of the type that can occur in encephalitis, and hypoxic or anoxic neuronal damage that can result from apnea, respiratory arrest or cardiac arrest, and anoxia caused by drowning, brain surgery or trauma (such as concussion or spinal cord shock).

In some embodiments, said disease, condition or disorder caused or associated with oxidative stress are selected from the group consisting of cancer, oxidative neurological disorders, free radical associated diseases, ischemia, ischemic reperfusion injury, inflammatory diseases, systemic lupus erythematosis, myocardial ischemia or infarction, cerebrovascular accidents, operative ischemia, traumatic hemorrhage, spinal cord trauma, Down's syndrome, Crohn's disease, autoimmune diseases, cataract formation, uveitis, emphysema, gastric ulcers, oxygen toxicity, neoplasia, undesired cellular apoptosis, radiation sickness, and any combinations thereof.

In a further aspect the invention provides a compound as defined in all aspects and embodiments of a compound of the invention, for use in the treatment of oxidative associated diseases, disorder or condition of the CNS.

In another aspect the invention provides a compound as defined in all aspects and embodiments of a compound of the invention, for use in preventing, arresting, or treating neurological damage in a subject suffering from at least one disease, disorder or condition selected from Parkinson's disease, Alzheimer's disease and HIV dementia; autoimmune neurodegeneration, hypoxic or anoxic neuronal damage, respiratory arrest or cardiac arrest, anoxia caused by drowning and brain surgery or trauma.

In a further aspect the invention provides a compound as defined in all aspects and embodiments of a compound of the invention, for use in the treatment of an ischemic or neurodegenerative disease in the central nervous.

In some embodiments of a compound for use above, said ischemic or neurodegenerative disease is selected from the group consisting of: an ischemic infarct, Alzheimer's disease, Parkinson's disease, and human immunodeficiency virus dementia, Down's syndrome, and heart disease or any combinations thereof.

In a further aspect the invention encompasses a use of a compound of the invention, as described herein above in all aspects and embodiments of a compound of the invention, for the manufacture of a medicament (or a pharmaceutical composition).

The invention further provides a use of a compound of the invention, as described herein above in all aspects and embodiments of a compound of the invention, for the manufacture of a medicament for the treatment of at least one condition, disease or disorder selected from the group consisting of psychiatric disorders, inflammation, oxidation associated conditions, rheumatoid arthritis, cardiovascular diseases, obesity, diabetes and associated disorders and symptoms, emesis and nausea, ischemic/reperfusion injury associated with myocardial, liver or renal diseases, hypoxia/ischemia injury, neuronal damage due to neurological diseases or injury, cancer and resistance to cancer chemotherapy, epilepsy and convulsions, and any condition or symptom associated therefrom.

In another aspect the invention provides a use of a compound of the invention, as described herein above in all aspects and embodiments of a compound of the invention, for the manufacture of a medicament for reduction of oxidative stress.

In yet another aspect the invention provides a use of a compound of the invention, as described herein above in all aspects and embodiments of a compound of the invention, for the manufacture of a medicament for the treatment of any disease, condition or disorder caused by or associated with oxidative stress.

In some embodiments of a use above, said disease, condition or disorder caused or associated with oxidative stress are selected from the group consisting of cancer, oxidative neurological disorders, free radical associated diseases, ischemia, ischemic reperfusion injury, inflammatory diseases, systemic lupus erythematosis, myocardial ischemia or infarction, cerebrovascular accidents, operative ischemia, traumatic hemorrhage, spinal cord trauma, Down's syndrome, Crohn's disease, autoimmune diseases, cataract formation, uveitis, emphysema, gastric ulcers, oxygen toxicity, neoplasia, undesired cellular apoptosis, radiation sickness, and any combinations thereof.

In a further aspect the invention provides a use of a compound according to the invention (as defined in any of the aspects and embodiments of a compound of the invention), for the manufacture of a medicament for the treatment of oxidative associated disease, disorder or condition of the CNS.

In another aspect the invention provides a use of a compound according to the invention (as defined in any of the aspects and embodiments of a compound of the invention), for the manufacture of a medicament for preventing, arresting, or treating neurological damage in a subject suffering from at least one disease, disorder or condition selected from Parkinson's disease, Alzheimer's disease and HIV dementia; autoimmune neurodegeneration, hypoxic or anoxic neuronal damage, respiratory arrest or cardiac arrest, anoxia caused by drowning and brain surgery or trauma and any combinations thereof.

In a further aspect the invention provides a use of a compound according to the invention (as defined in any of the aspects and embodiments of a compound of the invention), for the manufacture of a medicament for the treatment of an ischemic or neurodegenerative disease in the central nervous.

In some embodiments of a use above, said ischemic or neurodegenerative disease is selected from the group consisting of: an ischemic infarct, Alzheimer's disease, Parkinson's disease, and human immunodeficiency virus dementia, Down's syndrome, and heart disease or any combinations thereof.

The invention also provides a method of treating a condition, disease, disorder or symptom associated with inflammation in a subject in need thereof, said method comprising administering to said subject an effective amount of at least one compound of the invention, as described herein above in all aspects and embodiments of a compound of the invention.

The invention further encompasses a method of reduction of oxidative stress in a tissue or an organ of a subject in need thereof, said method comprising administering to said subject an effective amount of at least one compound of the invention, as described herein above in all aspects and embodiments of a compound of the invention.

According to a further aspect the invention provides a method of treating any disease, condition or disorder caused by or associated with oxidative stress a subject in need thereof, said method comprising administering to said subject an effective amount of at least one compound of the invention, as described herein above in all aspects and embodiments of a compound of the invention.

In some embodiments of a method above, said disease, condition or disorder caused by or associated with oxidative stress are selected from the group consisting of cancer, oxidative neurological disorders, free radical associated diseases, ischemia, ischemic reperfusion injury, inflammatory diseases, systemic lupus erythematosis, myocardial ischemia or infarction, cerebrovascular accidents, operative ischemia, traumatic hemorrhage, spinal cord trauma, Down's syndrome, Crohn's disease, autoimmune diseases, cataract formation, uveitis, emphysema, gastric ulcers, oxygen toxicity, neoplasia, undesired cellular apoptosis, radiation sickness, and others.

In a further aspect the invention provides a method for the treatment of oxidative associated disease, disorder or condition of the CNS in a subject, comprising administering to said subject a therapeutically effective amount of a compound of the invention (as defined in any of the aspects and embodiments of a compound of the invention).

In another aspect the invention provides a method for preventing, arresting, or treating neurological damage in a subject suffering from at least one disease, disorder or condition selected from Parkinson's disease, Alzheimer's disease and HIV dementia; autoimmune neurodegeneration, hypoxic or anoxic neuronal damage, respiratory arrest or cardiac arrest, anoxia caused by drowning and brain surgery or trauma, comprising administering to said subject a therapeutically effective amount of a compound of the invention (as defined in any of the aspects and embodiments of a compound of the invention).

In a further aspect the invention provides a method of treating an ischemic or neurodegenerative disease in the central nervous system of a subject, comprising administering to the subject a therapeutically effective amount of a compound of the invention (as defined in any of the aspects and embodiments of a compound of the invention).

In some embodiments of a method above, said ischemic or neurodegenerative disease is selected from the group consisting of: an ischemic infarct, Alzheimer's disease, Parkinson's disease, and human immunodeficiency virus dementia, Down's syndrome, and heart disease or any combinations thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Example 1

Fluorination of Cannabidiol (HU-474)

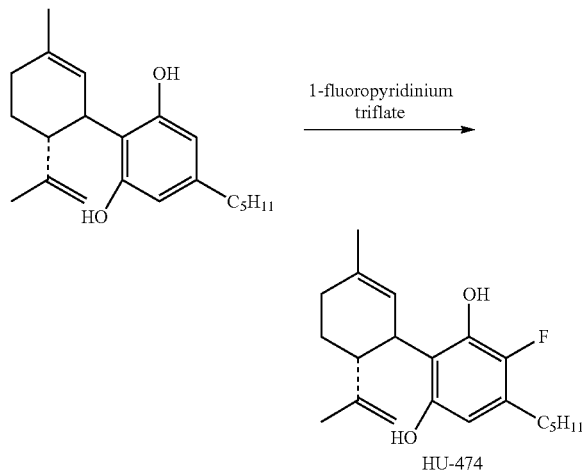

Figure 1:
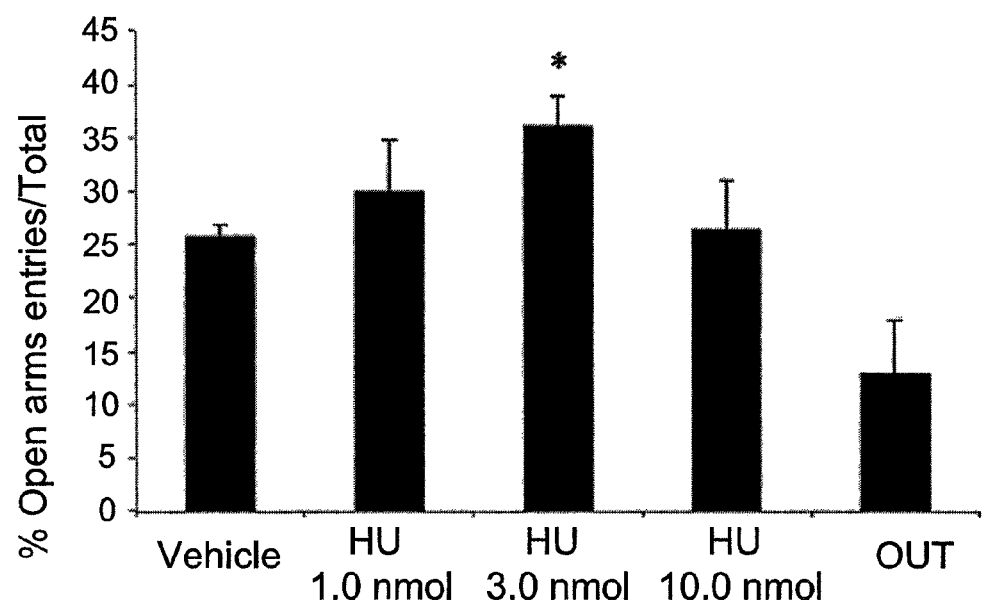
FIG. 1 shows the effects of HU-475 (a compound of the invention 1, 3 and 10 nmol, n=8-9 animals/group) and vehicle (n=7) microinjected into the dorsolateral periaqueductal gray of rats submitted to the elevated plus maze. Data expressed as means±SEM of the percentage of entries onto the open arms. * indicates significant difference from vehicle ($p<0.05$).

To a solution of cannabidiol (942 mg, 3 mmol) in dry $CH_2Cl_2$ (42 mL) was added 1-fluoropyridinium triflate (742 mg, 3 mmol) and the reaction mixture was stirred at ambient temperature overnight. After dilution with $CH_2Cl_2$ the mixture was washed with saturated aqueous solution of $NaHCO_3$. The organic layer was separated, dried over $MgSO_4$ and evaporated. The oil obtained was chromatographed on a silica gel column (75 g). Elution with 2% ether in petroleum ether gave the compound 4'-fluoro-cannabidiol (HU-474) as a solid (300 mg, 27%) m.p. 59-61° C. $^1$H NMR (300 MHz, $CDCl_3$) δ 6.17 (1H, s, arom.) 5.52 (1H, s), 4.56 (1H, s), 4.44 (1H, s), 3.92 (1H, s), 2.50 (2H, b), 2.19-2.05 (2H, b), 1.77 (3H, s), 0.86 (3H, t). MS, m/e=332 (M$^+$).

Example 2

Fluorination of Cannabidiol Diacetate (HU-475)

Step A

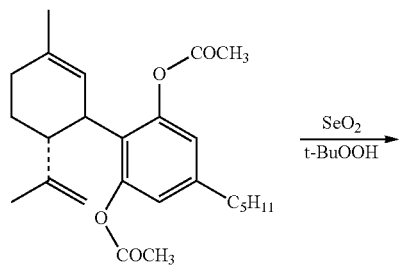

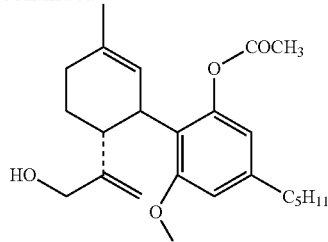

10-hydroxy-cannabidiol diacetate

To a suspension of $SeO_2$ (219 mg, 2 mmol) and t-BuOOH (2.8 mL, 70% in water) in $CH_2Cl_2$ (7 mL) was added a solution of cannabidiol diacetate (2 g, 5 mmol) in $CH_2Cl_2$ (10 mL). After stirring the mixture at ambient temperature overnight, it was washed with saturated aqueous solution of $NaHCO_3$ followed by a saturated solution of $NaHSO_3$. The organic layer was separated, dried over $MgSO_4$, filtered and evaporated. The oil obtained was purified on a silica gel column (50 g). Elution with 13% ether in petroleum ether gave the required compound 10-hydroxy-cannabidiol diacetate (670 mg, 40%) as oil. $^1$H NMR (300 MHz, $CDCl_3$), δ 6.7 (2H, s), 5.17 (1H, s), 4.99, (1H, s), 4.87 (1H, s), 3.70-3.80 (2H m), 3.53-3.58 (1H, m), 2.52-2.57 (2H, t J=7.6 Hz), 2.39-2.48 (1H d J=5.1 Hz), 2.18 (6H, s), 2.06 (1H, s), 2.0 (1H, s), 1.58 (1H, s), 1.25-1.31 (4H, m), 0.86-0.90 (3H t, J=6.45 Hz).

Step B

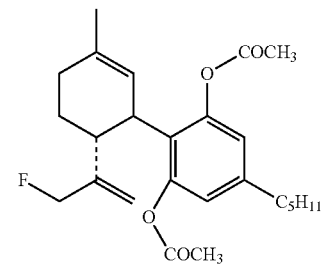

The alcohol (414 mg, 1 mmol) in dry $CH_2Cl_2$ (4 mL) was added under $N_2$ atmosphere to an ice-cold solution of DAST (0.18 mL, 1.5 mmol). After 15 min at 0° C. solid $Na_2CO_3$ (125 mg, 1 mmol) was added. The organic phase was then washed twice with cold 1 M aqueous $Na_2CO_3$ solution, followed by water. The organic layer was separated, dried over $MgSO_4$, filtered and evaporated. The resulting crude material was purified on a silica gel column (20 g) using 10% ether in petroleum ether to provide the fluorinated product 10-fluoro-cannabidiol diacetate (HU-475) (77.5 mg, 18.6%). $^1$H NMR (300 MHz, CDCl$_3$) δ 6.74 (2H, s), 5.21 (1H, s), 5.01 (1H, s), 4.87 (1H, s), 4.60 (1H, s), 4.50 (1H, s), 3.6 (1H, b), 2.73 (1H, t), 2.57 (2H, t), 2.21 (6H, s), 2.08-1.59 (8H, ms), 1.32 (3H, s), 0.90 (3H, t). MS, m/e=416 (M$^+$).

Example 3

In Vivo Effect of HU-474 in Mice and HU-475 in Rats

1. Animals

Male Wistar rats (220-250 g) and Swiss mice (25-30 g) originated from the Central Animal Farm of the School of Medicine of Ribeirão Preto (FMRP-USP) were maintained in groups of five animals per box (41×33×17 cm) in a temperature controlled room (24±2° C.) with a 12×12 h light-dark cycle. They received water and food ad libitum throughout the study period.

2. Compositions

HU-474 (1, 3 and 10 mg/kg) was administered intraperitoneally (IP) in mice at 10 mL/kg volume and HU-475 (1, 3 and 10 nmol) was injected intra-dlPAG in rats. Both drugs were dissolved in 2% Tween 80 in sterile saline.

3. Stereotaxic Surgery (HU-475)

Rats were submitted to a stereotaxic surgery to unilaterally implant cannulae (9.0 mm, 0.6 mm OD) into the dlPAG (coordinates: lateral: −1.9 mm; depth: −4.3 mm; angle: 16° from lambda; Paxinos and Watson, 2005), fixed to the skull with acrylic cement (Campos & Guimarães, 2008). The surgeries were performed under anesthesia with tribromoethanol 2.5% (10.0 mL/kg, IP) and immediately after the animals received Veterinary Pentabiotic (0.2 mL, intramuscular) and analgesic (Banamine, 1.0 mL/kg, subcutaneous) to prevent infections and decrease post-surgical pain. After surgery, animals underwent a recovery period of 5-7 days before the behavioral tests.

4. Microinjection (HU-475)

Animals received unilateral microinjections of vehicle or HU-475 into the dlPAG before being submitted to the behavioral tests. To this aim, microneedles (10.0 mm, 0.3 mm OD), connected to a microsyringe (Hamilton, USA, 10 mL) through a segment of polyethylene (P10) were inserted into the guide cannulae. Solutions were injected with the help of an infusion pump (KD Scientific, USA). A 0.2 µL solution volume was injected over 1 min After the injections, the needles remained inserted in the cannulae for additional 30 seconds to prevent drug reflux (Campos & Guimarães, 2008).

5. Apparatus 5.1 Elevated Plus-Maze (EPM) Rats

The wood EPM used to perform the experiments was located in a sound attenuated and temperature controlled room (23° C.), with one incandescent light (40 W) placed 1.3 m away from the maze. The apparatus consists of two opposing open arms (50×10 cm) without side walls, perpendicular to two enclosed arms (50×10×40 cm), with a central platform common to all arms (10×10 cm). The apparatus is elevated 50 cm above the ground and has an acrylic edge (1 cm) in the open arms to prevent animal falls. In this model, rodents naturally avoid the open arms, exploring more extensively the enclosed arms. Anxiolytic drugs increase the exploration in open arms without affecting the number of enclosed arms entries, which is usually used to assess general exploratory activity (File, 1992). Ten minutes after the last injection the animal was placed on the central platform of the maze with the head facing one of the enclosed arms. The test lasted for 5 min and was recorded. The animal behavior was analyzed with the help of the Anymaze Software (version 4.5, Stoelting). This software indicates the location of the animal in the EPM and automatically calculates the percentage of entries (Peo) and time spent in the open arms (Pto) and the number of entries in the enclosed arms (EA). Animals were only considered to enter an open or enclosed arm when 90% of their bodies were inside the region. All experiments were performed in the morning period (8 to 12 a.m.).

5.2 Elevated Plus-Maze (EPM) Mice

Similar to 5.1 except that the each arm measured 30×5 cm.

5.3 Forced Swimming Test (FST) Mice

Animals were individually submitted for 6 min of forced swimming in glass cylinders (height 25 cm, diameter 17 cm) containing 10 cm of water. The mice were videotaped and the immobility time (characterized by slow movements necessary to avoid drowning) was measured during the last 4-min period. The water was changed after each trial to maintain the temperature at 23-25° C. and to prevent the influence of alarm substances (Zanelati et al., 2010).

6. Histology-Rats

After the behavioral tests animals were anesthetized with chloral hydrate 4% (10 mL/kg) and perfused with saline 0.9%. Brains were removed and kept in formalin solution 10% for 3-7 days. Soon after, brains were cut into 50-µm thick sections in a cryostat (Cryocut 1800). The injection sites were identified in diagrams from the Paxinos and Watson's atlas (Paxinos and Watson, 2005). Rats receiving injections outside the aimed area were included in a separate group (out group).

7. Statistical Analysis

Results from HU-475 and HU-474 tests in the elevated plus maze were analyzed by Kruskal-Wallis followed by Mann-Whitney tests. Data from animals tested in the FST were analyzed by one-way ANOVA followed by Duncan test.

Results.

HU-475. The drug increased the percentage of entries ($X^2=9.66$, DF=4, $p<0.05$, FIG. 1) and tended to do the same ($X^2=8.5$, DF=4, $p=0.075$, FIG. 2) with the percentage of time spent into the open arms. No effect was found in the number of enclosed arm entries.

Figure 2:
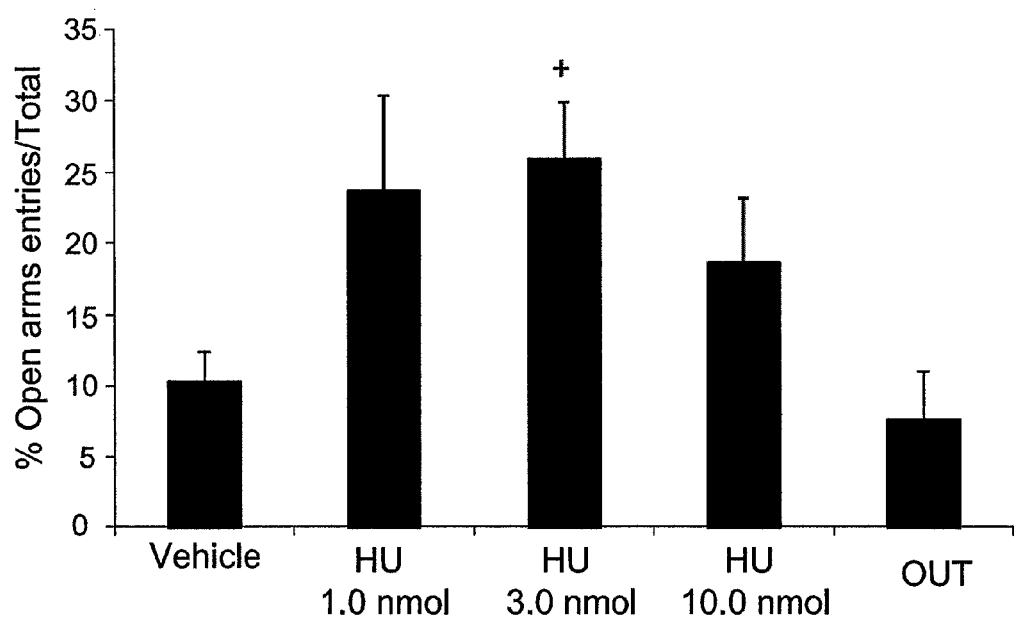
FIG. 2 shows the effects of HU-475 (a compound of the invention 1, 3 and 10 nmol, n=8-9 animals/group) and entries onto vehicle (n=7) microinjected into the dorsolateral periaqueductal gray of rats submitted to the elevated plus maze. Data expressed as means±SEM of the percentage of time spent in the open arms. + indicates a trend ($p<0.1$) for a difference from vehicle.

FIG. 1 shows the effects of HU-475 (1, 3 and 10 nmol, n=8-9 animals/group) and vehicle (n=7) microinjected into the dorsolateral periaqueductal gray of rats submitted to the elevated plus maze. Results from animals that received the dose of 3 nmol outside the target region are shown in the OUT group (n=6). Data expressed as means±SEM of the percentage of entries onto the open arms. * indicates significant difference from vehicle ($p<0.05$). FIG. 2 shows the effects of HU-475 (1, 3 and 10 nmol, n=8-9 animals/group) and vehicle (n=7) microinjected into the dorsolateral periaqueductal gray of rats submitted to the elevated plus maze. Results from animals that received the dose of 3 nmol outside the target region are shown in the OUT group. Data expressed as means±SEM of the percentage of time spent in the open arms. + indicates a trend ($p<0.1$) for a difference from vehicle.

Figure 3:
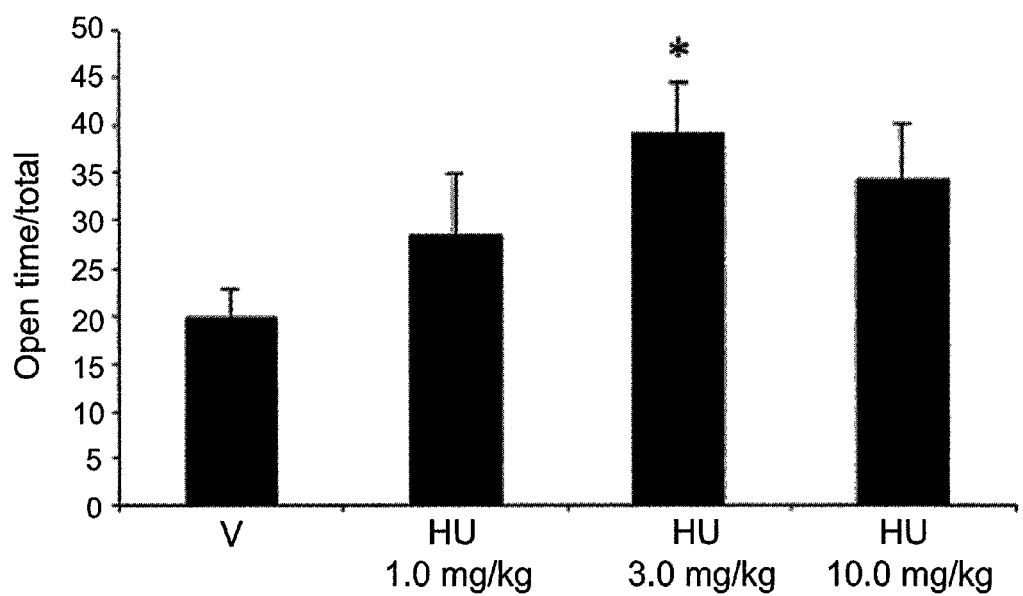
FIG. 3 shows the effects of HU-474 (a compound of the invention 1, 3 and 10 mg/kg n=6-8 animals/group) and vehicle (n=7) in mice tested in the elevated plus maze. Data expressed as means±SEM of the percentage of time in the open arms. * indicates significant difference from vehicle.
Figure 4:
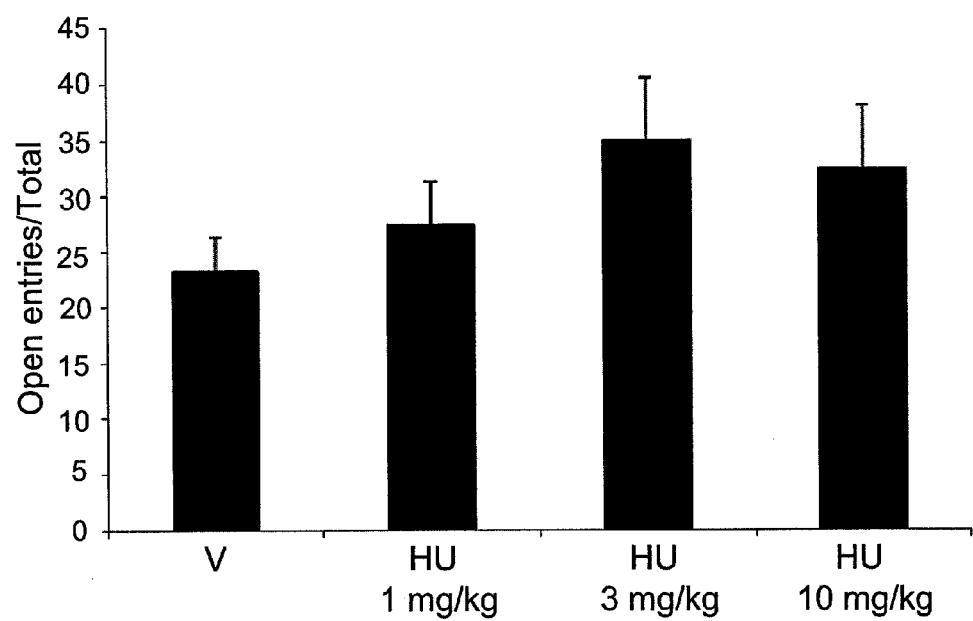
FIG. 4 shows the effects of HU-474 (a compound of the invention 1, 3 and 10 mg/kg n=6-8 animals/group) and vehicle (n=7) in mice tested in the elevated plus maze. Data expressed as means±SEM of the percentage of entries onto the open arms.
Figure 5:
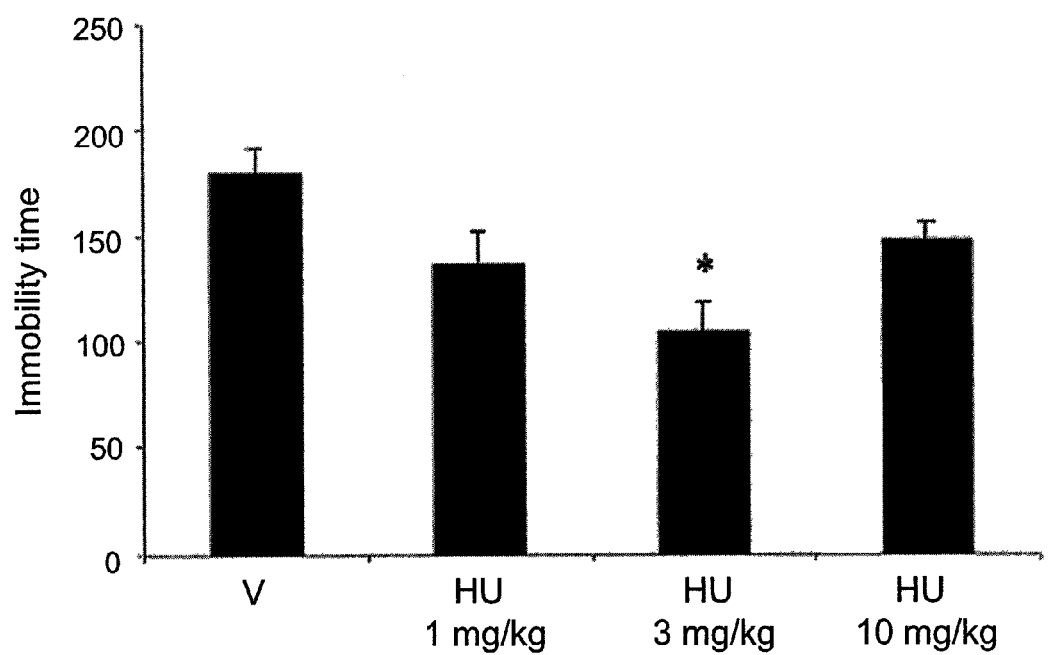
FIG. 5 shows the effects of HU-474 (a compound of the invention 1, 3 and 10 mg/kg n=6-8 animals/group) and vehicle (n=7) in mice immobility time (s) showed by mice tested in the FST. Data expressed as means±SEM. * indicates significant difference from vehicle.

HU-474. The drug increased the percentage of time spent in the open arms of the pEPM ($X^2=8.13$, DF=3, $p<0.05$, FIG. 3. No effect was found in the percentage of entries onto these same arms (FIG. 4) and the number of enclosed arms entries. The drug also decreased immobility time in the FST ($F3,2=4.06$, $p=0.019$, FIG. 5) at the dose of 3 m/kg. The doses of 1 and 10 mg/kg were ineffective. FIG. 3 shows the effects of HU-474 (1, 3 and 10 mg/kg n=6-8 animals/group)

and vehicle (n=7) in mice tested in the elevated plus maze. Data expressed as means±SEM of the percentage of time in the open arms. * indicates significant difference from vehicle. FIG. 4 shows the effects of HU-474 (1, 3 and 10 mg/kg n=6-8 animals/group) and vehicle (n=7) in mice tested in the elevated plus maze. Data expressed as means±SEM of the percentage of entries onto the open arms. FIG. 5 shows the effects of HU-474 (1, 3 and 10 mg/kg n=6-8 animals/group) and vehicle (n=7) in mice immobility time (s) showed by mice tested in the FST. Data expressed as means±SEM. * indicates significant difference from vehicle.

Discussion (Comparative Results with CBD)

Intra-dlPAG injection of HU-475 increased exploration of the open arms of the EPM without changing the number of enclosed arm entries. This indicates an anxiolytic-like effect (File, 1991) and was similar to that produced by CBD using the same paradigm, including a bell-shaped dose-response curve. However, the effective dose of CBD was 30 nmol (doses tested: 15, 30 and 60 nmol), same dose produced an anxiolytic-like effect in the Vogel punished licking test (Campos & Guimarães, 2008). In this model, therefore, HU-475 was 10 times more potent that CBD.

Systemic administration of HU-474 induced anxiolytic-like effects in mice tested the EPM with a characteristic bell-shaped dose-response curve. The effective dose was 3 mg/kg. In comparison with CBD, Onaivi et al. (1990) in a study conducted with a different mice strain (ICR), observed similar anxiolytic effects at the doses of 1 and 10 mg/kg i.p. (with the 10 mg/kg of CBD being more effective). HU-474 also decrease immobility time in mice tested in the forced swimming test, a model sensitive to antidepressant drugs. CBD also produced an antidepressant-like effect in Swiss mice tested in this model at the dose of 30 mg/kg i.p. (doses tested 3, 10, 30 and 100 mg/kg). Therefore, in this model HU-474 was 10 times more potent than CBD.

Example 4

Pre-Pulse Inhibition Test (HU-474)

1. Animals

The experiments were performed using male C57BL/6J mice weighting 25-30 g. The animals were maintained throughout the experimental period under standard laboratory conditions with free access to water and food will be used.

2. Compositions

HU-474 (3 and 10 mg/kg) was dissolved in 2% Tween 80 in sterile saline (vehicle). MK-801 (a NMDA antagonist, 0.5 mg/kg, Sigma, USA) was dissolved in saline. Drugs were administered intraperitoneally (ip) at 10 mL/kg volume.

3. Experimental Procedure

The animals (n=9-11/group) received i.p. administration of vehicle or HU-474 (3 and 10 mg/kg) followed, 30 minutes later, by saline or MK-801 (0.5 mg/kg), resulting in the following experimental groups: vehicle+saline, HU 10+saline, vehicle+MK-801, HU 3+MK-801, HU 10+MK-801. The animals were submitted to PPI test 20 minutes after the last drug injection.

4. Pre-Pulse Inhibition (PPI)

The PPI was carried out in three consecutive steps. The first consisted of an acclimation period during which no stimulus was presented. In the second step, called habituation, only the stimulus that triggers the startle (pulse) was presented. The step that assessed the inhibition of startle response pulse consisted of 64 random presentations of the different stimuli: (i) pulse (white noise) 105 dB at 20 ms, (II) pre-pulse (pure tone frequency of 7 kHz) 80, 85 and 90 dB at 10 ms, (III) followed by pre-pulse 100 ms interval between them and (IV) zero (no stimulus). During this session the stimuli are presented at regular intervals of 30 s, 8 presentations of each stimulus. The percentage of the PPI was expressed as the percent inhibition of startle amplitude in response to multiple presentations of the pulse preceded by pre-pulse (PP), depending on the amplitude of the response only to the pulse (P), which was obtained in the following formula: % PPI=100−((PP/P)×100). Using this formula 0% represents no difference between the amplitude of startle triggered only by the pulse or pulse preceded by the pre-pulse and therefore no pre-pulse inhibition. This transformation was performed in order to reduce the statistical variability attributable to differences between animals and represents a direct measure of pre-pulse inhibition (Issy et al., 2009).

5 Statistical Analysis

The percentage of PPI was analyzed by repeated measures MANOVA with the treatment as the independent factor and the prepulse intensity (80, 85 and 90 dB) as repeated measure. Duncan's post hoc test ($P<0.05$) was used to identify differences revealed by significant MANOVA.

Results

Figure 6:
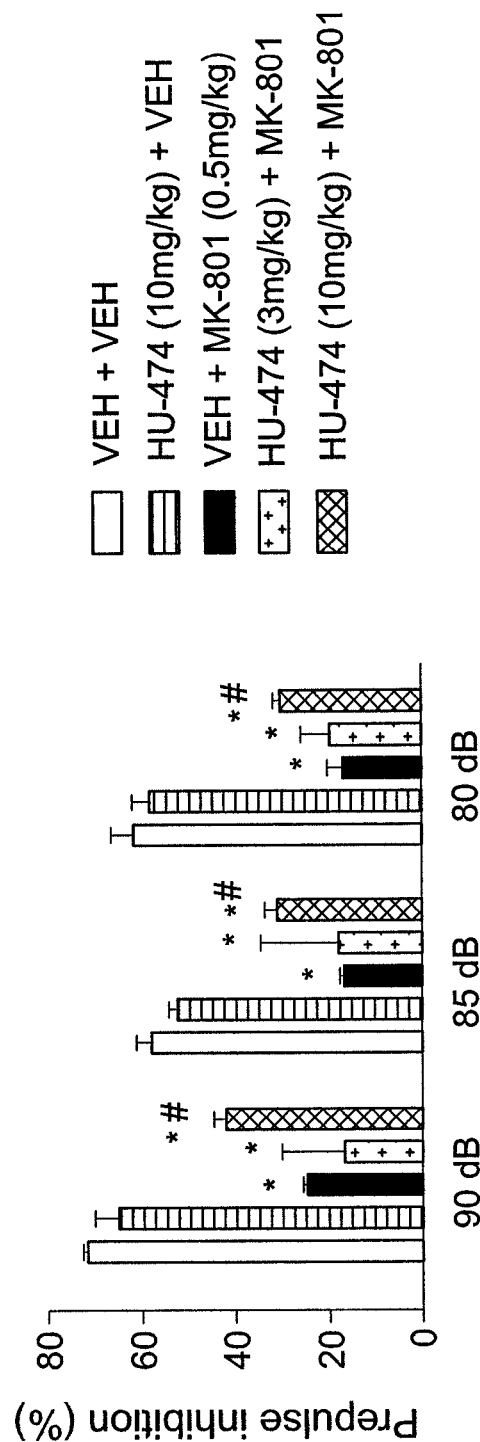
FIG. 6 shows the effects of HU-474 (3 and 10 mg/kg i.p.) in mice on the impairment of PPI induced by MK-801 (M0.5 mg/kg). Results are expressed as means±SEM. * indicates significant difference from vehicle-vehicle, # significant difference from vehicle-MK group.

The MANOVA revealed significant main effects of pre-pulse intensity ($F_{2,70}=23.53$, $P<0.05$) and treatment ($F_{4,35}=45.42$, $P<0.05$) but no interaction between prepulse intensity and treatment ($F8,70=1.08$, $P>0.05$). MK-801 promoted significant PPI disruption for all prepulse intensities tested ($P<0.05$, Duncan post-test). HU-474 (10 mg/kg) attenuated MK-801 PPI disruption in all prepulse intensities tested ($P<0.05$, FIG. 6). FIG. 6 shows the effects of HU-474 (3 and 10 mg/kg i.p.) in mice on the impairment of PPI induced by MK-801 (M0.5 mg/kg). Results show the percent inhibition of startle amplitude in response to multiple presentations of the pulse preceded by pre-pulse and are expressed as means±SEM. * indicates significant difference from vehicle-vehicle, # significant difference from vehicle-MK group.

Discussion (Comparison with CBD results)

A single CBD administration (5 mg/kg, I.p.) attenuated PPI deficits caused by MK801 (0.3-1 mg/kg, i.p.) in Swiss mice (Long et al., 2006). Observe that in this case the effective CBD dose (the authors also tested 1 and 15 mg/kg) was lower than that observed in HU-474 (10 mg/kg).

The above experimental procedure is also performed with 30 mg/kg dose of HU-474. HU-474 is also tested in dopamine-based models (hyperlocomotion induced by d-amphetamine). CBD effective doses are 30 and 60 mg/kg (Swiss mice). 30 mg/kg dose are able to attenuate the hyper-locomotion induced by MK801 (Moreira and Guimarães, 2005).

The invention claimed is:

1. A compound having the general formula (V):

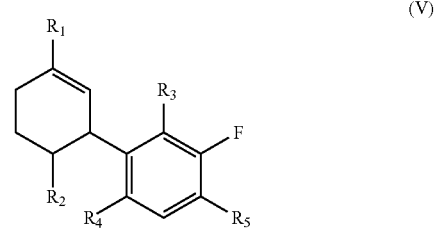

wherein
R$_1$ is selected from straight or branched C$_1$-C$_8$ alkyl, straight or branched C$_2$-C$_{10}$ alkenyl, straight or branched C$_2$-C$_{10}$ alkynyl, —C(=O)R$_8$, —C(=O)OR$_9$, each optionally substituted by at least one F;

R$_2$ is selected from straight or branched C$_1$-C$_8$ alkyl, straight or branched C$_2$-C$_{10}$ alkenyl, straight or branched C$_2$-C$_{10}$ alkynyl, each optionally substituted by at least one F;

R$_3$ and R$_4$ are each independently selected from H, straight or branched C$_1$-C$_5$ alkyl, —OR$_{10}$, —C=OR$_{11}$, —OC=OR$_{12}$, provided that at least one of R$_3$ and R$_4$ is different than H;

R$_5$ is selected from a straight or branched C$_5$-C$_{12}$ alkyl, a straight or branched C$_5$-C$_9$ alkoxy, a straight or branched C$_1$-C$_7$ ether, each being optionally substituted by at least one substituent selected from —OH, —NH$_3$, straight or branched C$_1$-C$_5$ amine, halogen, phenyl, aryl, heteroaryl, cycloalkyl and heterocycloalkyl;

R$_8$, and R$_9$ are independently selected from H, OH, straight or branched C$_1$-C$_5$ alkyl, straight or branched C$_1$-C$_5$alkoxy, —NH$_3$, straight or branched C$_1$-C$_5$ amine;

R$_{10}$ is selected from H, a straight or branched C$_1$-C$_5$ alkyl; and

R$_{11}$ and R$_{12}$ are independently selected from H, OH, straight or branched C$_1$-C$_5$ alkl straight or branched C$_1$-C$_5$ alkoxy, —NH$_3$, straight or branched C$_1$-C$_5$ amine.

2. A composition comprising at least one compound according to claim 1.

3. A method of treating a condition, disease, disorder or symptom associated with a psychiatric disease or condition selected from the group consisting of: anxiety, stress, depression, schizophrenia, panic, substance abuse withdrawal symptoms, reward-facilitating effect of addictive substances, memory loss, and psychotic-like symptoms associated with the use of substance abuse, in a subject in need thereof, said method comprising administering to said subject an effective amount of at least one compound according to claim 1.

4. The compound according to claim 1, wherein R$_1$ is a straight or branched C$_1$-C$_8$ alkyl; R$_3$ and R$_4$ are each independently —OR$_{10}$; R$_{10}$ is selected from H, a straight or branched C$_1$-C$_5$ alkyl.

5. The compound according to claim 1, wherein R$_1$ is a straight or branched C$_1$-C$_8$ alkyl, and R$_3$ and R$_4$ are each OH.

6. The compound according to claim 1, wherein R$_5$ is a straight or branched C$_5$-C$_{12}$ alkyl.

7. The compound according to claim 1, wherein R$_1$ is selected from straight or branched C$_1$-C$_8$ alkyl, straight or branched C$_2$-C$_{10}$ alkenyl, straight or branched C$_2$-C$_{10}$ alkynyl, each substituted by F.

8. The compound according to claim 1, wherein R$_2$ is selected from straight or branched C$_1$-C$_8$ alkyl, straight or branched C$_2$-C$_{10}$ alkenyl, straight or branched C$_2$-C$_{10}$ alkynyl, each substituted by F.

9. The compound of claim 1, wherein the compound is:

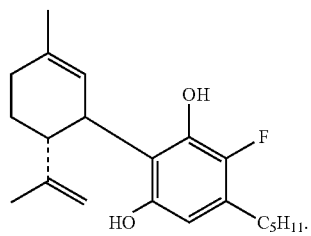

10. The compound of claim 1, wherein the compound is:

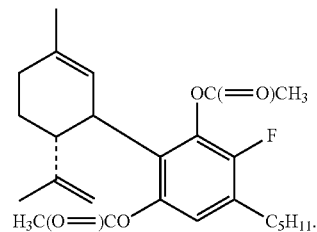

* * * * *